United States Patent [19]
Cox

[11] Patent Number: 5,976,182
[45] Date of Patent: *Nov. 2, 1999

[54] BALLOON-EXPANDABLE, CRUSH-RESISTANT LOCKING STENT AND METHOD OF LOADING THE SAME

[75] Inventor: Daniel L. Cox, Palo Alto, Calif.

[73] Assignee: Advanced Cardiovascular Systems, Inc., Santa Clara, Calif.

[*] Notice: This patent is subject to a terminal disclaimer.

[21] Appl. No.: 09/097,345

[22] Filed: Jun. 15, 1998

Related U.S. Application Data

[63] Continuation of application No. 08/943,875, Oct. 3, 1997, Pat. No. 5,766,239.

[51] Int. Cl.$^6$ ........................................... A61F 2/06
[52] U.S. Cl. .................. 623/1; 623/11; 623/12; 606/191; 606/194; 606/195; 606/198
[58] Field of Search .................. 623/1, 11, 12; 606/191, 194, 195, 198

[56] References Cited

U.S. PATENT DOCUMENTS

| | | |
|---|---|---|
| 4,994,071 | 2/1991 | MacGregor . |
| 5,575,816 | 11/1996 | Rudnick et al. ............ 623/1 |
| 5,733,330 | 3/1998 | Cox ............................ 623/1 |

FOREIGN PATENT DOCUMENTS

| | | |
|---|---|---|
| 0 423 916 A1 | 4/1991 | European Pat. Off. . |
| WO 96 41592 | 12/1996 | WIPO . |

*Primary Examiner*—Paul B. Prebilic
*Assistant Examiner*—Choon P. Koh
*Attorney, Agent, or Firm*—Fulwider Patton Lee & Utecht, LLP

[57] ABSTRACT

An intraluminal, crush resistant stent for implantation in a body lumen is disclosed. The crush resistant stent is made from a base section having a plurality of resilient, parallel, coplanar struts having a zig-zag configuration extending therefrom wherein the zig-zag struts are curved and pass through corresponding slots in the base section to form a continuous, cylindrical hoop. Each zig-zag strut has an amplitude that decreases when the zig-zag strut is placed under tension and an amplitude that increases when the zig-zag strut is unstressed or is placed under compression. Accordingly, each zig-zag strut can be pulled through the respective slot in the base section, but under compression the zig-zag struts assume the larger amplitude and cannot pass through the corresponding slot thereby maintaining the diameter of the stent constant.

12 Claims, 2 Drawing Sheets

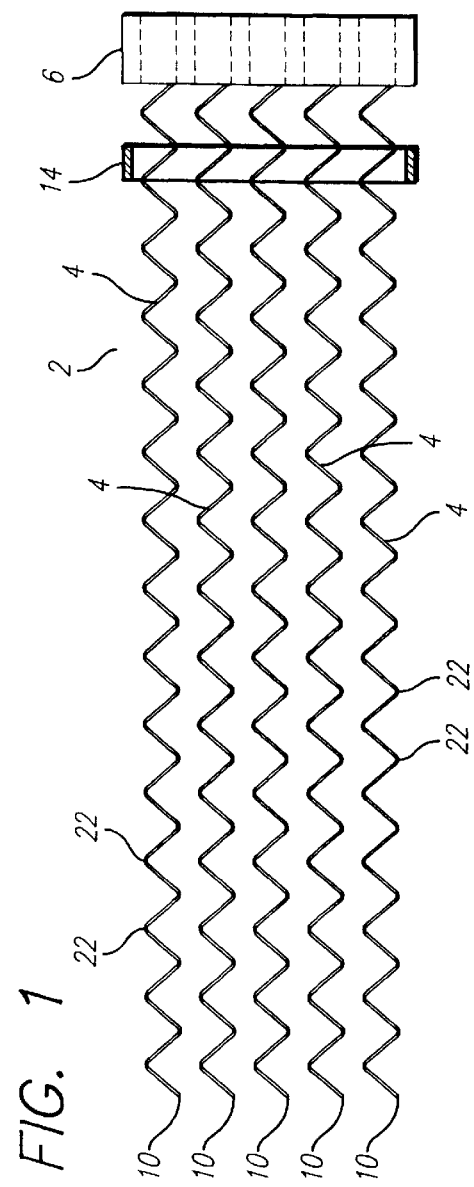
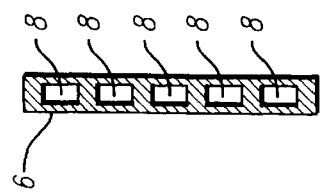
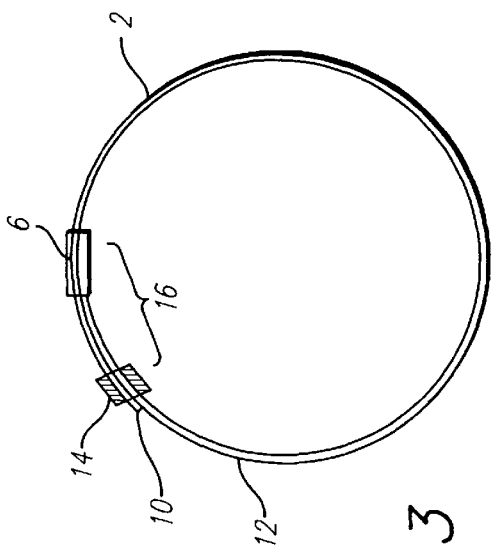
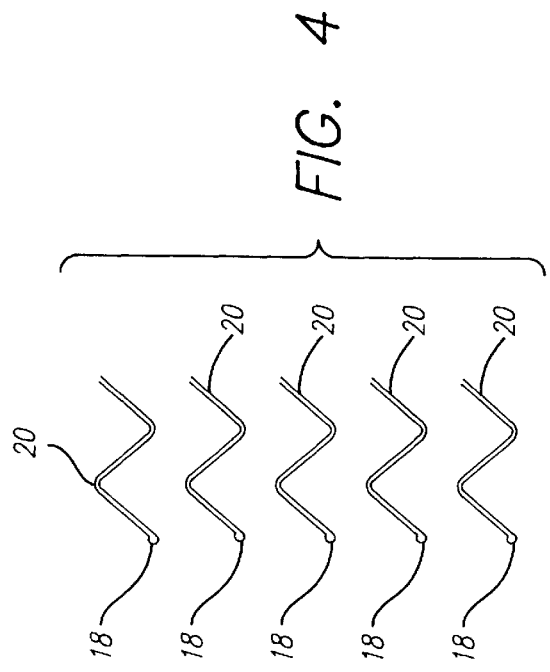

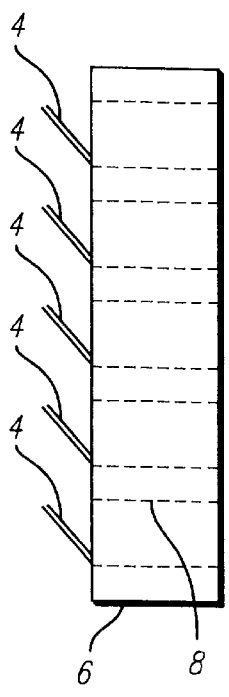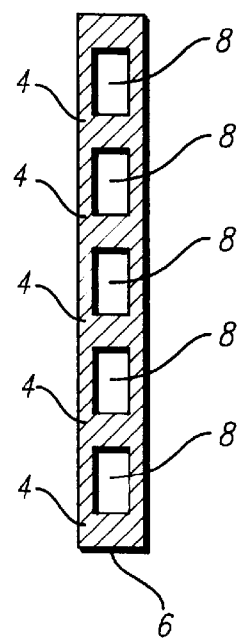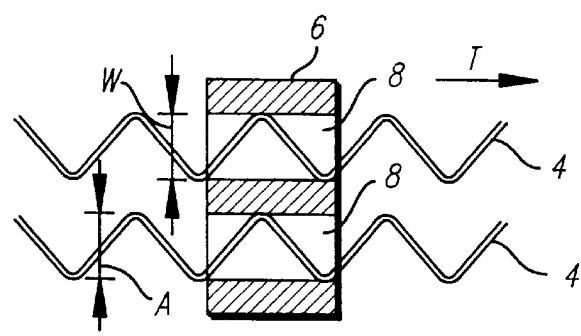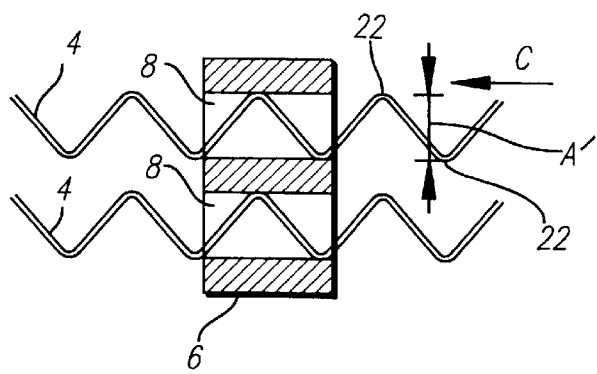

BALLOON-EXPANDABLE, CRUSH-RESISTANT LOCKING STENT AND METHOD OF LOADING THE SAME

This is a continuation application of co-pending application Ser. No. 08/943,875, filed on Oct. 3, 1997, issuing as U.S. Pat. No. 5,766,239, entitled "Balloon-Expandable, Crush Resistant Locking Stent And Method Of Loading The Same," whose entire contents are hereby incorporated by reference.

BACKGROUND OF THE INVENTION

The present invention relates generally to expandable, intraluminal vascular grafts, generally referred to as stents. More particularly, the present invention relates to a balloon expandable, crush resistant locking stent.

Expandable intraluminal vascular grafts, generally called stents, are adapted to be implanted into a patient's body lumen, such as a blood vessel, to maintain the patency of the vessel. These devices are frequently used in the treatment of atherosclerotic stenosis in blood vessels, especially after percutaneous transluininal coronary angioplasty (PTCA) procedures, to reduce the likelihood of restenosis of a blood vessel.

In expandable stents that are delivered with expandable catheters, such as a balloon catheter, the stents are positioned over the balloon portion of the catheter and expanded from a reduced diameter to an enlarged diameter greater than or equal to the artery wall, by inflating the balloon. Stents of this type can be expanded and held in the enlarged diameter by deformation of the stent as taught in, for example, U.S. Pat. No. 4,733,665 to Palmaz; by engagement of the stent walls with respect to one another as in, for example, U.S. Pat. Nos. 4,740,207 to Kreamer, 4,877,030 to Beck et al., and 5,007,926 to Derbyshire; and by one-way engagement of the stent walls together with endothelial growth into the stent as shown in U.S. Pat. No. 5,059,211 to Stack et al.

A number of conventional stents in order to be easily expandable have a rolled up cylinder construction. For example, U.S. Pat. No. 5,443,500 to Sigwart discloses an intravascular stent intended for implantation in a stenotic area or zone of obstruction of a blood vessel consisting of a flat sheet that is perforated to form a reticulated or lattice type structure with undeformable links and made of malleable material. The sheet is temporarily rolled up and locked in a spiral with a relatively small diameter on a deflated balloon mounted on the end of a catheter and is held in the rolled up state by a tie laced into overlapping links. Once the device is in place in the restricted area of the blood vessel to be treated and after the tie is removed, the rolled sheet is expanded to a desired diameter by inflating the balloon.

U.S. Pat. No. 5,423,885 to Williams discloses an expandable, balloon catheter delivered intravascular stent having a plurality of protrusions on its outer surface for engaging the artery walls in which it is disposed. The stent has a rolled up sheet construction, wherein apertures are formed in the stent body from the space vacated in the body by the material forming the protrusions. When the stent is expanded by the balloon catheter, the protrusions engage both the apertures and the artery walls to lock the stent into the expanded diameter.

U.S. Pat. No. 5,306,286 to Stack et al. discloses an expandable stent having a rolled up mesh construction. The stent can be reduced in diameter by a rolling motion while still having a cylindrical configuration on its outer surface for uniform engagement with a vessel wall. The rolled up, absorbable stent is mounted on either a balloon catheter, a mechanically expandable catheter, or other suitable stent delivery assembly. By expanding the distal balloon of the catheter or mechanically expandable distal end portion of the mechanically expandable catheter, the stent is expanded so as to engage the vessel wall.

U.S. Pat. No. 5,192,307 to Wall discloses a stent-like prosthesis which is formed of plastic or sheet metal and is expandable or contractible for placement. The stent may selectively be biased towards a closed position and lockable in an open position or biased in an open position and lockable in a closed position. In the former case, the stent is put into place in its collapsed condition, then forcibly expanded by a balloon to the desired locked condition. In the latter case, the stent may be held by a pin or the like in its collapsed condition, and the pin removed to allow the stent to assume its open position. The locking function is performed by one or more hooks formed into the wall which engage complementary recesses formed in an opposing wall to mechanically interlock the rolled up sheet forming the stent.

U.S. Pat. No. 5,441,515 to Khosravi et al. discloses an intravascular stent comprising a cylindrical sheet having overlapping edges that interlock. The edges having a series of protrusions and apertures that interlock and ratchet as the stent expands to an open position to support a section of arterial wall. The stent may be expanded by a balloon catheter or it may be self-expanding. A plurality of retaining members keep the stent open, and a buckle fastening member is used in one embodiment.

Copending U.S. Ser. No. 08/512,300, filed Aug. 8, 1995, entitled "Ratcheling Stent," is a divisional application of U.S. Pat. No. 5,441,515 to Khosravi, relating to a ratcheting stent having a rolled, cylindrical sheet construction.

There is, however, still a need for an expandable, crush resistant locking stent that has a durable, crush proof construction with a simplified locking mechanism. The crush proof aspect of the stent minimizes the possibility of an embolism in the vessel if, after implantation, the stent collapses as a result of, for example, an accidental chest trauma or impact on a vessel close to the skin such as the carotid arteries.

SUMMARY OF THE INVENTION

The present invention provides a method and apparatus directed to an intraluminal, crush resistant stent for implantation in a body lumen comprising a plurality of resilient, substantially parallel and coplanar struts having a zig-zag configuration and extending from a base section. Each zig-zag strut defines a large amplitude when the strut is an unstretched state and a small amplitude when the strut is in a stretched state. The invention further comprises a plurality of slots formed within the base section corresponding to each of the zig-zag struts, each slot having a width that is less than the large amplitude. The plurality of struts are coplanar and collectively curved and, when stretched to the small amplitude, pass through the slots of the base section forming a continuous, cylindrical hoop shape stent.

In the preferred embodiment, the present invention includes a zig-zag pattern which can have a variety of cross-sections including round, square, rectangular, elliptical, or triangular shapes. Each zig-zag strut extends from a locking fixture to which it is either attached or made from the same block of material. The ends of each zig-zag strut can be terminated in a variety of configurations. Each zig-zag strut fits through a corresponding slot or opening in the base section or similar locking fixture to complete the cylindrical hoop.

The present invention stent is loaded onto a delivery catheter or the like. In its continuous hoop form, the stent receives the deflated balloon of a balloon catheter in its incomplete hoop form. The zig-zag struts can be wound onto the balloon catheter, and by pulling the zig-zag struts through the respective slots and releasing the tension, the stent is locked onto the balloon catheter.

The ends of the zig-zag struts may be wound continuously around the balloon and can be held in place with an optional protective sheath. With the protective sheath in place, the balloon catheter and stent, in their reduced diameter form, are transported through the vasculature.

Once positioned at the stenotic region, the stent is deployed by first exposing the stent by withdrawing the protective sheath, and then inflating the underlying balloon. The zig-zag struts undergo circumferential tensioning from the expanding balloon and assume the smaller amplitude. The smaller amplitude permits the zig-zags to pass through the slots in the base section, thus allowing the hoop diameter to increase along with the inflating balloon. Further inflation of the balloon and stent implants the stent within the body lumen. Deflating the balloon facilitates withdrawal of the catheter and completion of the stent delivery process.

The stent locks with the base section because the amplitude of each zig-zag strut, being larger than the respective slot width when the zig-zag strut is in the unstressed or untensioned state, abuts against the slot. Conversely, when the stent is being deployed, each zig-zag strut is stretched circumferentially and the amplitude of each zig-zag decreases accordingly until it fits through the width of the slot. At that point, the zig-zag strut passes unobstructed through the slot and the stent undergoes an increase in its diameter.

When the stent is squeezed under a compression load, the stent locks in place because the squeezing action increases the amplitude of each zig-zag to a large amplitude that is too large to fit through its corresponding slot in the base section. Hence, the diameter of the stent cannot be decreased. If the stent is made from a resilient material, the material in combination with the zig-zag struts abutting the smaller width slots, provide a crush resistant characteristic to the stent.

In addition, the present invention stent can be made to be crush resistant by using a shape-memory, nickel-titanium alloy as the base material. The stent could be more user friendly by stabilizing the shape memory of in the state at which it is wound onto the balloon. Importantly, the present invention nickel-titanium stent would be particularly well suited for carotid arteries (or other vessels close to the skin surface) where crush resistance is very important due to possible accidental trauma to the neck area of the patient.

These and other aspects and advantages of the present invention will become apparent from the following detailed description and the accompanying drawings, which illustrate by way of example the features of the invention.

BRIEF DESCRIPTION OF THE DRAWINGS

FIG. 1 is a top plan view of a preferred embodiment of the invention illustrating the plurality of coplanar zig-zag struts extending from a base section.

FIG. 2 is an end view of an exemplary embodiment of the base section shown in FIG. 1.

FIG. 3 is an end view of the present invention after the plurality of zig-zag struts have been bent into a curve and inserted through the corresponding slots in the base section to form a hoop.

FIG. 4 is a plan view of an alternative embodiment of the ends of the zig-zag struts.

FIG. 5 is a plan view of the base section shown in FIG. 1.

FIG. 6 is an end view of the base section shown in FIG. 5, exposing the slots and the point of attachment of the zig-zag struts to the base section.

FIGS. 7(a) and (b) are sectional views of two zig-zag struts passing through corresponding slots in the base section wherein FIG. 7(a) shows the struts under circumferential tension, and FIG. 7(b) shows the struts under compression.

DETAILED DESCRIPTION OF THE PREFERRED EMBODIMENTS

The present invention is directed to an intraluminal, crush resistant stent for implantation in a body lumen and a method for loading a crush resistant stent onto the balloon portion of a catheter. While the present invention is described in detail as applied to intravascular stents, those skilled in the art will appreciate that the present invention can be applied to other surgical procedures and internal organs. Moreover, the stent may be deployed in a body lumen through a variety of devices, including but not limited to balloon catheters and specialized stent delivery catheters.

FIG. 1 depicts a plan view of a preferred embodiment of the present invention stent 2. Stent 2 has a plurality of parallel zig-zag or saw-tooth profile struts 4 that are also preferably coplanar. Each zig-zag strut 4 extends from base section 6. Zig-zag struts 4 are formed as part of the base section 6 or they can be bonded, welded, or mechanically attached thereto through processes known in the art. As their name implies, zig-zag struts 4 are wavy along their respective lengths wherein the waviness is comprised of a number of individual bend 22. Zig-zag struts 4 are preferably resilient and should have some slight shape-memory as well. Furthermore, zig-zag struts 4 can have a variety of cross-sections including round (cylindrical), square, elliptical, or triangular shapes. Preferably, zig-zag strut 4 should have a rectangular cross-section to facilitate bending.

The plan view of FIG. 1 shows base section 6 having a rectangular shape, although other shapes and dimensions are possible based on design requirements. As best seen in FIG. 2, which provides an end view of the base section 6, there are a plurality of slots 8 that correspond to the number of zig-zag struts 4.

At the terminus of each zig-zag strut 4 is end 10. Starting at the coplanar ends 10, the entire plane defined by zig-zag struts 4 can be curled collectively to form cylindrical hoop 12, as best seen in the end view of FIG. 3. To close or complete hoop 12, ends 10 must pass through corresponding slots 8 in base section 6. Optional retainer 14 having a generally rectangular loop shape permits passage of zig-zag struts 4 therethrough; after the hoop shape is achieved, overlapping portion 16 can also pass therethrough and be held in place.

Overlapping portion 16 is thus held against the outside diameter of hoop 12 as seen in FIG. 3. This prevents ends 10 from extending radially away from hoop 12 due to the resilience in the material of zig-zag struts 4.

FIG. 4 is a partial plan view of an alternative embodiment showing enlarged ends 18 on zig-zag struts 20. Enlarged ends 18 help prevent zig-zag struts 20 from traumatizing the vessel wall. They are also conveniently pinched between a technician's fingers for pulling zig-zag struts 20 through slots 8.

Once stent 2 is formed by curling zig-zag struts 4 into base section 6 to form cylindrical hoop 12 as seen in FIG. 3, it is ready for use. First, stent 2 must be loaded onto a delivery catheter or similar device. Specifically, stent 2 of the present invention is placed over a stent delivery balloon catheter (not shown).

Second, the catheter is percutaneously introduced into a vessel, over a previously positioned guidewire in an over-the-wire angioplasty catheter system, and tracked by a fluoroscope, until the balloon portion and associated stent 2 are positioned at the point where stent 2 is to be deployed. Third, the balloon portion (not shown), which is positioned directly beneath stent 2, is inflated and stent 2 is expanded by the balloon portion from a reduced diameter form to an expanded diameter form. Fourth, after stent 2 has been expanded to its final expanded diameter, the underlying balloon is deflated and the catheter is withdrawn leaving stent 2 in place.

As is appreciated by those skilled in the art, stent 2 while being transported is of a sufficiently small reduced diameter so as to allow it to be readily transported through a vessel. In an alternative embodiment, a retractable sheath (not shown) can cover stent 2 to protect it during delivery to the deployment site, where the sheath is then retracted. Such protective sheaths for stents are known in the art.

FIGS. 5–7 provide more detailed views of the locking mechanism used in a preferred embodiment of the present invention. The locking mechanism, having base section 6, is an important feature when stent 2 is loaded onto the balloon catheter and the diameter of stent 2 is expanded during deployment thereof, and, when after implantation, stent 2 encounters external forces that might collapse an otherwise conventionally locked stent.

FIG. 5 is a plan view of the preferred embodiment base section 6 showing zig-zag struts 4 extending therefrom and a corresponding number of slots 8 therethrough. FIG. 6 is an end view showing the opposite end to that shown in FIG. 2. Ideally, zig-zag struts 4 as seen in FIG. 6 are aligned in a coplanar manner as are slots 8, although the two planes are preferably offset slightly from each other. The offset planes allow zig-zag struts 4 to be curled around and to pass through their respective slots 8.

FIGS. 7(a) and (b) illustrate the preferred embodiment locking mechanism of the present invention in operation. In particular, FIG. 7(a) shows two zig-zag struts 4 under circumferential tension as indicated by arrow T. Zig-zag struts 4 under this tensile force are stretched and pulled through slots 8 within base section 6.

In particular, under tension, zig-zag struts 4 assume a small amplitude A, which is smaller than width W of slots 8. This change is due to the resilience in the zig-zag strut material, which enables bends 22 to flatten out slightly under tension.

FIGS. 3 and 7(a) depict the process of loading the present invention stent 6 onto a balloon catheter wherein ends 10 are passed through the respective slots 8 and pulled to a diameter sufficiently small to fit over the outside diameter of the catheter balloon. Likewise, when stent 2 is deployed, the increasing diameter of the underlying catheter balloon places zig-zag struts 4 under tension causing them to assume small amplitude A. The small amplitude permits individual bends 22 to pass through their respective slots 8 unobstructed. In sum, the diameter of hoop 12 can decrease if zig-zag struts 4 are pulled on their ends 10, or it can increase with the increasing diameter of the catheter balloon undergoing inflation.

After implantation, the catheter balloon is deflated and withdrawn through processes known in the art. Without the outward expanding catheter balloon to circumferentially tension stent 2, it returns to the original, unstressed state and assumes large amplitude A'. Because large amplitude A' is greater than slot width W, bends 22 are obstructed from passing through. Hence, the diameter of hoop 12 is rigidly locked in place and cannot be changed.

Once stent 2 has been implanted, it may encounter external forces from the inner walls of the lumen or from physical trauma originating from outside the patient, which external forces tend to compress zig-zag struts 4 circumferentially. This is illustrated by arrow C in FIG. 7(b).

As mentioned above, in the unstressed state, zig-zag struts 4 assume large amplitude A' which cannot pass through slots 8. Under compression force C, the zig-zag struts might be compressed slightly and bends 22 might assume an even sharper angle and a corresponding large amplitude A' or greater. With large amplitude A' or greater, which is greater than width W of slot 8, bends 22 as shown in FIG. 7(b) are obstructed and again cannot pass through their respective slots 8 in base section 6. In fact, bends 22 on either side of base section 6 are locked in place. Consequently, the diameter of hoop 12 is held constant despite encountering the external force. This enables the present invention stent 2 to be crush resistant.

Stent 2 is preferably made from a crush resistant, shape-memory material such as a nickel-titanium alloy (NiTi). Compounds using NiTi are manufactured under the marks NITINOL™ and ELASTINITE™ and available from several sources. Stent 2 could be made more user friendly by stabilizing the shape of the NiTi alloy in the state at which it is wound into a hoop 12 to take advantage of the shape-memory capability of the material. The properties of shape-memory (pseudoelastic) NiTi are described in more detail in U.S. Pat. Nos. 4,665,906; 5,067,957; and 5,190,546 to J. Jervis which are incorporated herein in their entirety.

In an alternative embodiment, the longitudinal flexibility of the stent can be enhanced by constructing the stent from segments of three to five zig-zag struts and specifically joining these small segments together with a small connection of metal. In short, each zig-zag strut need not be a continuous piece of material but can be made from smaller individual segments.

The present invention stent can further be made from standard stent materials such as stainless steel, tantalum, etc. Also, the present invention stent may be made from a biodegradable or bioabsorbable material such as polymers of the linear aliphatic polyester and glycolide families. Other materials contemplated for the present invention stent include biocompatible polymers, such as of the type from the polyethylene, polyester, and polypropylene families and plastics such as a polymer from the linear aliphatic polyester family, such as poly(lactic acid), poly(glycolic acid), or polycaprolactone, and their associated copolymers, degradable polymers such as polyorthoester, polyanhydride, polydioxanone, and polyhydroxybutyrate.

It is recognized that other modifications can be made to the present invention without departing from the scope thereof. The specific dimensions and materials of construction are provided as examples and substitutes are readily contemplated which do not depart from the invention.

What is claimed is:

1. An intraluminal, crush resistant stent for implantation in a body lumen, comprising:

at least one resilient, zig-zag shaped strut curved to form a hoop, wherein each zig-zag has an amplitude that varies as the strut is stretched or relaxed;

a base section disposed on the hoop having an opening for receiving the strut therethrough to close the hoop, wherein the opening has a dimension sufficiently large to accommodate the amplitude entirely when the strut is stretched whereby the curved strut passes through the base section and stretching the strut minimizes the amplitude to pass through the opening, which stretching defines a diameter of the hoop.

2. The crush resistant stent of claim 1, wherein the amplitude of the stretched strut is smaller than a width of the opening.

3. The crush resistant stent of claim 1, wherein the stretched strut defines a small amplitude and an unstretched strut defines a large amplitude, and wherein the small amplitude is less than the large amplitude.

4. An intraluminal, crush resistant stent for implantation in a body lumen, comprising:

at least one resilient, zig-zag shaped strut curved to form a hoop, wherein each zig-zag has an amplitude that decreases or increases as the strut is stretched or relaxed, respectively;

a base section disposed on the hoop having an opening sized sufficiently large to accommodate the amplitude entirely as defined by the zig-zag strut when it is stretched and passed therethrough.

5. The crush resistant stent of claim 4, wherein the opening has a rectangular shape having a width dimension that is sufficiently large to accommodate the entire amplitude defined by the zig-zag strut when it is stretched.

6. The crush resistant stent of claim 4, wherein the opening has a depth sufficient to contain a full cycle of the zig-zag strut.

7. The crush resistant stent of claim 4, wherein the struts each includes a saw-tooth profile.

8. An intraluminal, crush resistant stent for implantation in a body lumen, comprising:

at least one resilient, zig-zag waveform strut having a proximal end and a free distal end, wherein the strut is curved to form a hoop, and wherein each zig-zag waveform has an amplitude that decreases or increases as the strut is stretched or relaxed, respectively;

a base section extending from the proximal end, having at least one opening for passing the distal end of the strut therethrough to close the hoop, wherein the opening has an interior dimension that simultaneously engages adjacent maximum and minimum peak amplitudes of the waveform when the strut is stretched.

9. The crush resistant stent of claim 8, wherein the stent includes a plurality of zig-zag waveforn struts each curled to be concentric with each other, and wherein the base section includes a plurality of openings corresponding to each zig-zag waveform strut.

10. The crush resistant stent of claim 8, wherein the opening in the base section has a depth approximating one cycle of the zig-zag waveform.

11. The crush resistant stent of claim 8, wherein the stent includes a shape-memory alloy.

12. The crush resistant stent of claim 8, wherein the plurality of zig-zag waveforms are in phase.

* * * * *